US010766924B2

(12) United States Patent
Ichii et al.

(10) Patent No.: US 10,766,924 B2
(45) Date of Patent: Sep. 8, 2020

(54) AFFINITY SUPPORT AND METHOD FOR ISOLATING IMMUNOGLOBULIN

(71) Applicants: JSR CORPORATION, Minato-ku (JP); JSR LIFE SCIENCES CORPORATION, Minato-ku (JP)

(72) Inventors: Takashi Ichii, Minato-ku (JP); Satoshi Nakamura, Minato-ku (JP); Jun-ichi Yasuoka, Minato-ku (JP); Kaori Itaya, Minato-ku (JP); Tomonori Shiotani, Minato-ku (JP)

(73) Assignees: JSR CORPORATION, Minato-ku (JP); JSR LIFE SCIENCES CORPORATION, Minato-ku (JP)

( * ) Notice: Subject to any disclaimer, the term of this patent is extended or adjusted under 35 U.S.C. 154(b) by 276 days.

(21) Appl. No.: 15/745,855

(22) PCT Filed: Jul. 27, 2016

(86) PCT No.: PCT/JP2016/071968
§ 371 (c)(1),
(2) Date: Jan. 18, 2018

(87) PCT Pub. No.: WO2017/018437
PCT Pub. Date: Feb. 2, 2017

(65) Prior Publication Data
US 2018/0222939 A1    Aug. 9, 2018

(30) Foreign Application Priority Data

Jul. 28, 2015 (JP) ................. 2015-148670

(51) Int. Cl.
*C07K 1/22* (2006.01)
*B01J 20/32* (2006.01)
*B01J 20/289* (2006.01)
*G01N 30/88* (2006.01)

(52) U.S. Cl.
CPC ............... *C07K 1/22* (2013.01); *B01J 20/289* (2013.01); *B01J 20/321* (2013.01); *B01J 20/3204* (2013.01); *B01J 20/3219* (2013.01); *B01J 20/3248* (2013.01); *B01J 20/3255* (2013.01); *G01N 30/88* (2013.01); *G01N 2030/8831* (2013.01)

(58) Field of Classification Search
None
See application file for complete search history.

(56) References Cited

U.S. PATENT DOCUMENTS

| 2005/0221362 A1 | 10/2005 | Takiguchi et al. | |
|---|---|---|---|
| 2007/0106066 A1* | 5/2007 | Cherkasky | C12N 15/62 530/351 |
| 2008/0051555 A1* | 2/2008 | Iwakura | C07K 17/06 530/300 |
| 2013/0041135 A1* | 2/2013 | Tamori | B01D 15/3804 530/387.1 |
| 2015/0343420 A1 | 12/2015 | Onishi et al. | |
| 2016/0144294 A1 | 5/2016 | Shibuya et al. | |
| 2016/0159855 A1 | 6/2016 | Rodrigo et al. | |
| 2016/0159859 A1 | 6/2016 | Rodrigo et al. | |
| 2016/0207966 A1 | 7/2016 | Ander et al. | |
| 2017/0320922 A1 | 11/2017 | Ander et al. | |
| 2018/0244729 A1 | 8/2018 | Rodrigo et al. | |

FOREIGN PATENT DOCUMENTS

| CN | 102834415 A | 12/2012 |
|---|---|---|
| JP | 2-209155 A | 8/1990 |
| JP | 6-281638 A | 10/1994 |
| JP | 2005-292007 A | 10/2005 |
| JP | 2008-509883 A | 4/2008 |
| WO | 2006/001798 A1 | 1/2006 |
| WO | 2014/087937 A1 | 6/2014 |
| WO | 2014/181796 A1 | 11/2014 |
| WO | WO 2015/005859 A1 | 1/2015 |

OTHER PUBLICATIONS

Ainavarapu et al. "Contour lenghtt and refolding rate of a small protein controlled by engineered disulfide bonds" Biophysical Journal, 92 Jan. 2007, pp. 225-233 (Year: 2007).*

Sachiro Kakinoki, "Conformation Study of Proline-Related Polypeptides," Osaka Prefecture University Hakushi Ronbun Yoshi, Mar. 31, 2005, 8 pages (with partial English translation of p. 2).

International Search Report dated Nov. 1, 2016 in PCT/JP2016/071968 filed Jul. 27, 2016.

Combined Chinese Office Action and Search Report dated Aug. 28, 2019, in Patent Application No. 201680043673.2, 20 pages (with English translation).

Extended European Search Report dated Nov. 23, 2018 in Patent Application No. 16830542.3, 10 pages.

Shin-ichi Sato, et al., "Polyproline-Rod Approach to Isolating Protein Targets of Bioactive Small Molecules: Isolation of a New Target of Indomethacin", (JAGS) J. Am. Chem. Soc., vol. 129, No. 4, XP002490143, Jan. 31, 2007, pp. 873-880.

* cited by examiner

*Primary Examiner* — Daniel E Kolker
*Assistant Examiner* — James L Rogers
(74) *Attorney, Agent, or Firm* — Oblon, McClelland, Maier & Neustadt, L.L.P.

(57) ABSTRACT

To provide an affinity support in which a binding property of a ligand to a target substance is improved. The affinity support contains a solid phase support and a protein ligand, wherein the protein ligand is represented by formula (1): R—R$^1$ (1) wherein R represents a linker binding to the solid phase support, which contains a polyproline, and R$^1$ represents a protein showing an affinity to immunoglobulin, and the R is bound to a C terminal or an N terminal of an amino acid sequence in R$^1$.

10 Claims, No Drawings
Specification includes a Sequence Listing.

SEQUENCE LISTING

```
<160> NUMBER OF SEQ ID NOS: 11

<210> SEQ ID NO 1
<211> LENGTH: 58
<212> TYPE: PRT
<213> ORGANISM: Staphylococcus aureus
<220> FEATURE:
<223> OTHER INFORMATION: Protein A, B domain

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus
<220> FEATURE:
<223> OTHER INFORMATION: Protein A, Z domain

<400> SEQUENCE: 2

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 3
<211> LENGTH: 58
<212> TYPE: PRT
<213> ORGANISM: Staphylococcus aureus
<220> FEATURE:
<223> OTHER INFORMATION: Protein A, C domain

<400> SEQUENCE: 3

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45
```

```
Lys Lys Leu Asn Asp Ala Gln Ala Pro Lys
    50              55

<210> SEQ ID NO 4
<211> LENGTH: 242
<212> TYPE: PRT
<213> ORGANISM: Staphylococcus aureus

<400> SEQUENCE: 4

Ala Gln Gly Thr Val Asp Asn Lys Phe Asn Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Val Ser Lys Glu Ile
        35                  40                  45

Leu Ala Glu Ala Lys Lys Leu Asn Asp Ala Gln Ala Pro Lys Glu Phe
    50                  55                  60

Val Asp Asn Lys Phe Asn Lys Glu Gln Gln Asn Ala Phe Tyr Glu Ile
65                  70                  75                  80

Leu His Leu Pro Asn Leu Thr Glu Glu Gln Arg Asn Ala Phe Ile Gln
                85                  90                  95

Ser Leu Lys Asp Asp Pro Ser Val Ser Lys Glu Ile Leu Ala Glu Ala
            100                 105                 110

Lys Lys Leu Asn Asp Ala Gln Ala Pro Lys Glu Phe Val Asp Asn Lys
        115                 120                 125

Phe Asn Lys Glu Gln Gln Asn Ala Phe Tyr Glu Ile Leu His Leu Pro
    130                 135                 140

Asn Leu Thr Glu Glu Gln Arg Asn Ala Phe Ile Gln Ser Leu Lys Asp
145                 150                 155                 160

Asp Pro Ser Val Ser Lys Glu Ile Leu Ala Glu Ala Lys Lys Leu Asn
                165                 170                 175

Asp Ala Gln Ala Pro Lys Glu Leu Val Asp Asn Lys Phe Asn Lys Glu
            180                 185                 190

Gln Gln Asn Ala Phe Tyr Glu Ile Leu His Leu Pro Asn Leu Thr Glu
        195                 200                 205

Glu Gln Arg Asn Ala Phe Ile Gln Ser Leu Lys Asp Asp Pro Ser Val
    210                 215                 220

Ser Lys Glu Ile Leu Ala Glu Ala Lys Lys Leu Asn Asp Ala Gln Ala
225                 230                 235                 240

Pro Lys

<210> SEQ ID NO 5
<211> LENGTH: 243
<212> TYPE: PRT
<213> ORGANISM: Staphylococcus aureus

<400> SEQUENCE: 5

Ala Gln Gly Thr Val Asp Asn Lys Phe Asn Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Val Ser Lys Glu Ile
        35                  40                  45

Leu Ala Glu Ala Lys Lys Leu Asn Asp Ala Gln Ala Pro Lys Glu Phe
    50                  55                  60

Val Asp Asn Lys Phe Asn Lys Glu Gln Gln Asn Ala Phe Tyr Glu Ile
```

```
                65                  70                  75                  80
Leu His Leu Pro Asn Leu Thr Glu Glu Gln Arg Asn Ala Phe Ile Gln
                    85                  90                  95

Ser Leu Lys Asp Asp Pro Ser Val Ser Lys Glu Ile Leu Ala Glu Ala
                100                 105                 110

Lys Lys Leu Asn Asp Ala Gln Ala Pro Lys Glu Phe Val Asp Asn Lys
                115                 120                 125

Phe Asn Lys Glu Gln Gln Asn Ala Phe Tyr Glu Ile Leu His Leu Pro
130                 135                 140

Asn Leu Thr Glu Glu Gln Arg Asn Ala Phe Ile Gln Ser Leu Lys Asp
145                 150                 155                 160

Asp Pro Ser Val Ser Lys Glu Ile Leu Ala Glu Ala Lys Lys Leu Asn
                165                 170                 175

Asp Ala Gln Ala Pro Lys Glu Leu Val Asp Asn Lys Phe Asn Lys Glu
                180                 185                 190

Gln Gln Asn Ala Phe Tyr Glu Ile Leu His Leu Pro Asn Leu Thr Glu
                195                 200                 205

Glu Gln Arg Asn Ala Phe Ile Gln Ser Leu Lys Asp Asp Pro Ser Val
                210                 215                 220

Ser Lys Glu Ile Leu Ala Glu Ala Lys Lys Leu Asn Asp Ala Gln Ala
225                 230                 235                 240

Pro Lys Cys

<210> SEQ ID NO 6
<211> LENGTH: 241
<212> TYPE: PRT
<213> ORGANISM: Staphylococcus aureus

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
                20                  25                  30

Ser Leu Lys Asp Asp Pro Ser Val Ser Lys Glu Ile Leu Ala Glu Ala
                35                  40                  45

Lys Lys Leu Asn Asp Ala Gln Ala Pro Lys Glu Phe Val Asp Asn Lys
            50                  55                  60

Phe Asn Lys Glu Gln Gln Asn Ala Phe Tyr Glu Ile Leu His Leu Pro
65                  70                  75                  80

Asn Leu Thr Glu Glu Gln Arg Asn Ala Phe Ile Gln Ser Leu Lys Asp
                85                  90                  95

Asp Pro Ser Val Ser Lys Glu Ile Leu Ala Glu Ala Lys Lys Leu Asn
                100                 105                 110

Asp Ala Gln Ala Pro Lys Glu Phe Val Asp Asn Lys Phe Asn Lys Glu
            115                 120                 125

Gln Gln Asn Ala Phe Tyr Glu Ile Leu His Leu Pro Asn Leu Thr Glu
130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
                165                 170                 175

Pro Lys Glu Leu Val Asp Asn Lys Phe Asn Lys Glu Gln Gln Asn Ala
            180                 185                 190

Phe Tyr Glu Ile Leu His Leu Pro Asn Leu Thr Glu Glu Gln Arg Asn
```

```
                195                 200                 205
Ala Phe Ile Gln Ser Leu Lys Asp Asp Pro Ser Val Ser Lys Glu Ile
210                 215                 220

Leu Ala Glu Ala Lys Lys Leu Asn Asp Ala Gln Ala Pro Lys Lys Lys
225                 230                 235                 240

Lys

<210> SEQ ID NO 7
<211> LENGTH: 249
<212> TYPE: PRT
<213> ORGANISM: Staphylococcus aureus

<400> SEQUENCE: 7

Ala Gln Gly Thr Val Asp Asn Lys Phe Asn Lys Glu Gln Gln Asn Ala
1               5                   10                  15

Phe Tyr Glu Ile Leu His Leu Pro Asn Leu Thr Glu Glu Gln Arg Asn
                20                  25                  30

Ala Phe Ile Gln Ser Leu Lys Asp Asp Pro Ser Val Ser Lys Glu Ile
            35                  40                  45

Leu Ala Glu Ala Lys Lys Leu Asn Asp Ala Gln Ala Pro Lys Glu Phe
50                  55                  60

Val Asp Asn Lys Phe Asn Lys Glu Gln Gln Asn Ala Phe Tyr Glu Ile
65                  70                  75                  80

Leu His Leu Pro Asn Leu Thr Glu Glu Gln Arg Asn Ala Phe Ile Gln
                85                  90                  95

Ser Leu Lys Asp Asp Pro Ser Val Ser Lys Glu Ile Leu Ala Glu Ala
            100                 105                 110

Lys Lys Leu Asn Asp Ala Gln Ala Pro Lys Glu Phe Val Asp Asn Lys
        115                 120                 125

Phe Asn Lys Glu Gln Gln Asn Ala Phe Tyr Glu Ile Leu His Leu Pro
    130                 135                 140

Asn Leu Thr Glu Glu Gln Arg Asn Ala Phe Ile Gln Ser Leu Lys Asp
145                 150                 155                 160

Asp Pro Ser Val Ser Lys Glu Ile Leu Ala Glu Ala Lys Lys Leu Asn
                165                 170                 175

Asp Ala Gln Ala Pro Lys Glu Leu Val Asp Asn Lys Phe Asn Lys Glu
            180                 185                 190

Gln Gln Asn Ala Phe Tyr Glu Ile Leu His Leu Pro Asn Leu Thr Glu
        195                 200                 205

Glu Gln Arg Asn Ala Phe Ile Gln Ser Leu Lys Asp Asp Pro Ser Val
    210                 215                 220

Ser Lys Glu Ile Leu Ala Glu Ala Lys Lys Leu Asn Asp Ala Gln Ala
225                 230                 235                 240

Pro Lys Pro Pro Pro Pro Pro Cys
                245

<210> SEQ ID NO 8
<211> LENGTH: 252
<212> TYPE: PRT
<213> ORGANISM: Staphylococcus aureus

<400> SEQUENCE: 8

Ala Gln Gly Thr Val Asp Asn Lys Phe Asn Lys Glu Gln Gln Asn Ala
1               5                   10                  15

Phe Tyr Glu Ile Leu His Leu Pro Asn Leu Thr Glu Glu Gln Arg Asn
                20                  25                  30
```

```
Ala Phe Ile Gln Ser Leu Lys Asp Asp Pro Ser Val Ser Lys Glu Ile
            35                   40                  45

Leu Ala Glu Ala Lys Lys Leu Asn Asp Ala Gln Ala Pro Lys Glu Phe
 50                  55                  60

Val Asp Asn Lys Phe Asn Lys Glu Gln Gln Asn Ala Phe Tyr Glu Ile
 65                  70                  75                  80

Leu His Leu Pro Asn Leu Thr Glu Glu Gln Arg Asn Ala Phe Ile Gln
                 85                  90                  95

Ser Leu Lys Asp Asp Pro Ser Val Ser Lys Glu Ile Leu Ala Glu Ala
                100                 105                 110

Lys Lys Leu Asn Asp Ala Gln Ala Pro Lys Glu Phe Val Asp Asn Lys
            115                 120                 125

Phe Asn Lys Glu Gln Gln Asn Ala Phe Tyr Glu Ile Leu His Leu Pro
        130                 135                 140

Asn Leu Thr Glu Glu Gln Arg Asn Ala Phe Ile Gln Ser Leu Lys Asp
145                 150                 155                 160

Asp Pro Ser Val Ser Lys Glu Ile Leu Ala Glu Ala Lys Lys Leu Asn
                165                 170                 175

Asp Ala Gln Ala Pro Lys Glu Leu Val Asp Asn Lys Phe Asn Lys Glu
            180                 185                 190

Gln Gln Asn Ala Phe Tyr Glu Ile Leu His Leu Pro Asn Leu Thr Glu
        195                 200                 205

Glu Gln Arg Asn Ala Phe Ile Gln Ser Leu Lys Asp Asp Pro Ser Val
    210                 215                 220

Ser Lys Glu Ile Leu Ala Glu Ala Lys Lys Leu Asn Asp Ala Gln Ala
225                 230                 235                 240

Pro Lys Pro Pro Pro Pro Pro Pro Pro Cys
                245                 250

<210> SEQ ID NO 9
<211> LENGTH: 255
<212> TYPE: PRT
<213> ORGANISM: Staphylococcus aureus

<400> SEQUENCE: 9

Ala Gln Gly Thr Val Asp Asn Lys Phe Asn Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Val Ser Lys Glu Ile
        35                  40                  45

Leu Ala Glu Ala Lys Lys Leu Asn Asp Ala Gln Ala Pro Lys Glu Phe
 50                  55                  60

Val Asp Asn Lys Phe Asn Lys Glu Gln Gln Asn Ala Phe Tyr Glu Ile
 65                  70                  75                  80

Leu His Leu Pro Asn Leu Thr Glu Glu Gln Arg Asn Ala Phe Ile Gln
                 85                  90                  95

Ser Leu Lys Asp Asp Pro Ser Val Ser Lys Glu Ile Leu Ala Glu Ala
                100                 105                 110

Lys Lys Leu Asn Asp Ala Gln Ala Pro Lys Glu Phe Val Asp Asn Lys
            115                 120                 125

Phe Asn Lys Glu Gln Gln Asn Ala Phe Tyr Glu Ile Leu His Leu Pro
        130                 135                 140

Asn Leu Thr Glu Glu Gln Arg Asn Ala Phe Ile Gln Ser Leu Lys Asp
```

```
                145                 150                 155                 160
        Asp Pro Ser Val Ser Lys Glu Ile Leu Ala Glu Ala Lys Lys Leu Asn
                            165                 170                 175

Asp Ala Gln Ala Pro Lys Glu Leu Val Asp Asn Lys Phe Asn Lys Glu
                    180                 185                 190

Gln Gln Asn Ala Phe Tyr Glu Ile Leu His Leu Pro Asn Leu Thr Glu
                    195                 200                 205

Glu Gln Arg Asn Ala Phe Ile Gln Ser Leu Lys Asp Asp Pro Ser Val
                210                 215                 220

Ser Lys Glu Ile Leu Ala Glu Ala Lys Lys Leu Asn Asp Ala Gln Ala
        225                 230                 235                 240

Pro Lys Pro Pro Pro Pro Pro Pro Pro Pro Pro Pro Pro Pro Pro Cys
                            245                 250                 255

<210> SEQ ID NO 10
<211> LENGTH: 257
<212> TYPE: PRT
<213> ORGANISM: Staphylococcus aureus

<400> SEQUENCE: 10

Val Asp Asn Lys Phe Asn Lys Glu Gln Gln Asn Ala Phe Tyr Glu Ile
        1               5                   10                  15

Leu His Leu Pro Asn Leu Thr Glu Glu Gln Arg Asn Ala Phe Ile Gln
                    20                  25                  30

Ser Leu Lys Asp Asp Pro Ser Val Ser Lys Glu Ile Leu Ala Glu Ala
                    35                  40                  45

Lys Lys Leu Asn Asp Ala Gln Ala Pro Lys Glu Phe Val Asp Asn Lys
                50                  55                  60

Phe Asn Lys Glu Gln Gln Asn Ala Phe Tyr Glu Ile Leu His Leu Pro
        65                  70                  75                  80

Asn Leu Thr Glu Glu Gln Arg Asn Ala Phe Ile Gln Ser Leu Lys Asp
                        85                  90                  95

Asp Pro Ser Val Ser Lys Glu Ile Leu Ala Glu Ala Lys Lys Leu Asn
                    100                 105                 110

Asp Ala Gln Ala Pro Lys Glu Phe Val Asp Asn Lys Phe Asn Lys Glu
                    115                 120                 125

Gln Gln Asn Ala Phe Tyr Glu Ile Leu His Leu Pro Asn Leu Thr Glu
                    130                 135                 140

Glu Gln Arg Asn Ala Phe Ile Gln Ser Leu Lys Asp Asp Pro Ser Val
        145                 150                 155                 160

Ser Lys Glu Ile Leu Ala Glu Ala Lys Lys Leu Asn Asp Ala Gln Ala
                        165                 170                 175

Pro Lys Glu Leu Val Asp Asn Lys Phe Asn Lys Glu Gln Gln Asn Ala
                    180                 185                 190

Phe Tyr Glu Ile Leu His Leu Pro Asn Leu Thr Glu Glu Gln Arg Asn
                    195                 200                 205

Ala Phe Ile Gln Ser Leu Lys Asp Asp Pro Ser Val Ser Lys Glu Ile
                    210                 215                 220

Leu Ala Glu Ala Lys Lys Leu Asn Asp Ala Gln Ala Pro Lys Pro Pro
        225                 230                 235                 240

Pro Pro Pro Pro Pro Pro Pro Pro Pro Pro Pro Pro Pro Pro Pro Pro
                        245                 250                 255

Cys
```

```
<210> SEQ ID NO 11
<211> LENGTH: 259
<212> TYPE: PRT
<213> ORGANISM: Staphylococcus aureus

<400> SEQUENCE: 11

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Glu Phe Val Asp Asn Lys
50                  55                  60

Phe Asn Lys Glu Gln Gln Asn Ala Phe Tyr Glu Ile Leu His Leu Pro
65                  70                  75                  80

Asn Leu Thr Glu Glu Gln Arg Asn Ala Phe Ile Gln Ser Leu Lys Asp
                85                  90                  95

Asp Pro Ser Val Ser Lys Glu Ile Leu Ala Glu Ala Lys Lys Leu Asn
            100                 105                 110

Asp Ala Gln Ala Pro Lys Glu Phe Val Asp Asn Lys Phe Asn Lys Glu
            115                 120                 125

Gln Gln Asn Ala Phe Tyr Glu Ile Leu His Leu Pro Asn Leu Thr Glu
130                 135                 140

Glu Gln Arg Asn Ala Phe Ile Gln Ser Leu Lys Asp Asp Pro Ser Val
145                 150                 155                 160

Ser Lys Glu Ile Leu Ala Glu Ala Lys Lys Leu Asn Asp Ala Gln Ala
            165                 170                 175

Pro Lys Glu Leu Val Asp Asn Lys Phe Asn Lys Glu Gln Gln Asn Ala
            180                 185                 190

Phe Tyr Glu Ile Leu His Leu Pro Asn Leu Thr Glu Glu Gln Arg Asn
            195                 200                 205

Ala Phe Ile Gln Ser Leu Lys Asp Asp Pro Ser Val Ser Lys Glu Ile
210                 215                 220

Leu Ala Glu Ala Lys Lys Leu Asn Asp Ala Gln Ala Pro Lys Pro Pro
225                 230                 235                 240

Pro Pro Pro Pro Pro Pro Pro Pro Pro Pro Pro Pro Pro Pro Pro Pro
                245                 250                 255

Lys Lys Lys
```

AFFINITY SUPPORT AND METHOD FOR ISOLATING IMMUNOGLOBULIN

TECHNICAL FIELD

The present invention relates to an affinity support and a method for isolating immunoglobulin. In particular, the invention relates to a method for immobilizing a ligand to a support, capable of improving an immunoglobulin purification efficiency of an affinity support.

BACKGROUND ART

An affinity chromatography is a chromatography using a column filled with a ligand immobilization support in which a substance (ligand) capable of specifically binding a substance for the purpose of separation or purification is immobilized on an insoluble support. The affinity chromatography is used, for example, for separation or purification of bio-related substances such as protein or nucleic acid (Patent Literature 1). As the support for the affinity chromatography, for example, cross-linked particles of a carbohydrate chain, represented by agarose gel, and particles containing, as a main component, a synthetic polymer are used.

In the affinity chromatography, it is necessary to immobilize a ligand, which is a substance capable of specifically reacting with a target substance, to a support. For the purpose of immobilization of the ligand to the support, a method is frequently used in which the ligand is chemically bonded to various functional groups existing on a surface of the support through functional groups on the ligand. The ligands used for the affinity chromatography, however, generally have multiple functional groups, and the multiple functional groups are disorderly bound to functional groups on the support surface. This causes a problem in which the immobilized ligand can insufficiently effectively utilized in conventional affinity chromatography.

CITATION LIST

Patent Literature

Patent Literature 1: JP hei 6-281638 A

SUMMARY OF INVENTION

Technical Problem

A problem to be solved by the present invention is to provide a method which efficiently immobilizes a protein ligand on a surface of an affinity support, and maintains a binding capacity of the immobilized ligand to a target substance at a high rate.

Solution to Problem

In one embodiment, the present invention provides
an affinity support including a solid phase support and a protein ligand wherein
the protein ligand is represented by the following formula (1):

wherein
R represents a linker binding to the solid phase support, which contains a polyproline, and
$R^1$ represents a protein showing an affinity to immunoglobulin, and
the R is bound to a C terminal or an N terminal of an amino acid sequence in $R^1$.

The number of proline residues in the polyproline is preferably from 3 to 300.

The linker has preferably a length of from 0.9 nm to 91 nm.

In another embodiment, the present invention provides
an affinity support including a solid phase support and a protein ligand wherein
the protein ligand is represented by the following formula (1):

wherein
R represents a linker binding to the solid phase support and having a length of from 0.9 nm to 91 nm, and
$R^1$ represents a protein showing an affinity to immunoglobulin,
the R is bound to a C terminal or an N terminal of an amino acid sequence in $R^1$.

The linker preferably contains polyproline.

The number of proline residues in the polyproline is preferably from 3 to 300.

In one embodiment of the affinity support of the present invention, the linker contains an amino acid residue having an amino group or a thiol group at a terminal which binds to the solid phase support.

In one embodiment of the affinity support according to the present invention, the protein showing affinity to immunoglobulin contains an immunoglobulin-binding domain derived from an Fc-binding protein or Protein A.

In one embodiment of the affinity support according to the present invention, the protein showing affinity to immunoglobulin contains at least one immunoglobulin-binding domain selected from the group consisting of an immunoglobulin-binding domain consisting of an amino acid sequence represented by SEQ ID NO: 3, an immunoglobulin-binding domain consisting of a partial sequence of the amino acid sequence represented by SEQ ID NO: 3, and an immunoglobulin-binding domain consisting of an amino acid sequence having at least 70% identity to the amino acid sequence represented by SEQ ID NO: 3.

In one embodiment of the affinity support according to the present invention, the protein showing affinity to immunoglobulin contains two or more of the immunoglobulin-binding domains.

In one embodiment of the affinity support of the present invention, the solid phase support has a reactive group capable of binding a thiol group or an amino group.

In one embodiment of the affinity support of the present invention, the reactive group is an epoxy group.

In a further embodiment, the present invention provides a method for isolating immunoglobulin using the affinity support described above.

In a further embodiment, the present invention provides a method for producing an antibody preparation, using the affinity support described above.

In a further embodiment, the present invention provides
an affinity ligand comprising a linker R and a protein ligand $R^1$; wherein
the linker R contains polyproline,
$R^1$ represents an protein showing affinity to immunoglobulin, and
R is bound to a C terminal or an N terminal of an amino acid sequence in $R^1$.

Effect of the Invention

The affinity support of the present invention can immobilize a ligand protein to a support in a fixed orientation by binding the ligand protein to the support through a specific linker. As a result, in the affinity support of the present invention, modification and inadequate orientation of the ligand, caused by disorderly binding between the ligand and the support, is prevented, and the binding property of the ligand to a target substance can be improved. According to the present invention, therefore, an affinity ligand can be efficiently immobilized to the support surface, and the immobilized ligand can be efficiently utilized in the preparation of the target substance. The affinity support of the present invention has a high binding capacity of the immunoglobulin, and enable to carry out a purification process of the immunoglobulin in a low cost.

DESCRIPTION OF EMBODIMENTS

All patent literatures, non-patent literatures, and other publications cited herein are incorporated herein by reference in the entirety.

In the present specification, a sequence identity of an amino acid sequence or a nucleotide sequence is calculated by a Lipman-Pearson method (Science, 227, 1435-41, 1985). Specifically, analysis is carried out in a way in which Unit size to compare (ktup) is assumed as 2, using a Search homology program of a genetic information processing software, Genetyx-Win (Ver. 5.1.1: software development).

In the present specification, the phrase "at least 70% identity" for the amino acid sequence or the nucleotide sequence, refers to 70% or more identity, preferably 80% or more identity, more preferably 85% or more identity, still more preferably 90% or more identity, further more preferably 95% or more identity, still further more preferably 98% or more identity, even still further more preferably 99% or more identity.

In the present specification, the phrase "position corresponding to" on the amino acid sequence or the nucleotide sequence can be decided in a way in which a target sequence and a reference sequence (for example, an amino acid sequence represented by SEQ ID NO: 3) are aligned (alignment) so as to provide the maximum homology to conserved amino acid residues or nucleotides existing in each amino acid sequence or nucleotide sequence. The alignment can be carried out by using a known algorithm, and the procedure thereof is known by those skilled in the art. For example, the alignment can be manually performed based on the Lippmann-Pearson method described above, or the like, and can be performed using a Clustal W multiple alignment program (Thompson, J. D. et al., 1994, Nucleic Acids Res., 22: 4673-4680) which is default set. Alternatively, Clustal W2 or Clustal omega, which are revised Clustal W, can be used. Clustal W, Clustal W2, and Clustal omega can be utilized on web sites of, for example, European Bioinformatics Institute (EBI) [www.ebi.ac.uk/index.html] or DNA Data Bank of Japan (DDBJ), run by National Institute Genetics, [www.ddbj.nig.ac.jp/Welcome-j.html].

In the present specification, the term "protein" refers to every molecule having a peptide structural unit, and has a concept including, for example, mutants obtained by artificially modifying a partial fragment or an amino acid sequence of a natural protein. The protein may be modified by a substance derived from organism such as a carbohydrate chain or lipid, or a polymer such as polyethylene glycol.

In the present specification, Protein A refers to a Protein A which is a cell wall component of *Staphylococcus aureus*.

In the present specification, the term "immunoglobulin-binding domain" refers to a functional unit of polypeptide having an immunoglobulin binding activity alone. The term "immunoglobulin binding" herein refers to binding to a region other than a complementarity determining region (CDR) of the immunoglobulin molecule, particularly binding to at least an Fc fragment. Examples of the "immunoglobulin-binding domain" herein may include, preferably, immunoglobulin-binding domains derived from an Fc binding protein or Protein A. Examples of the immunoglobulin-binding domain derived from the Protein A may include A domain, B domain, C domain, D domain, and E domain of Protein A, Z domain which is a modified domain of B domain, and mutants derived therefrom. Examples of the mutant may include polypeptides having at least 70% identity in any of the A to E and Z domains and an amino acid sequence, and an immunoglobulin-binding capacity.

In the present specification, the term "protein showing affinity to immunoglobulin" or "immunoglobulin-binding protein" refers to a protein specifically showing affinity to immunoglobulin, and having immunoglobulin-binding capacity. Preferable one may include proteins having at least one, more preferably 2 or more "immunoglobulin-binding domains" described above.

1. Affinity Support

An affinity support according to one embodiment of the present invention contains a solid phase support and a protein ligand, and the protein ligand is represented by the following formula (1):

$$R—R^1 \quad (1)$$

wherein

R is a linker chemically binding the solid phase support;
$R^1$ is a protein showing affinity to immunoglobulin; and
the R is bound to a C terminal or an N terminal of an amino acid sequence in the $R^1$.

1.1. Support 1.1.1. Structure

The solid phase support contained in the affinity support of the present invention is preferably a water-insoluble substrate. The solid phase support may have a particulate shape, and the particle may be porous or nonporous. The particulate support may be used as a packed bed or in the state of suspension. The suspension state may include an expanded bed, and pure suspension, and the particles can freely move in this state. In cases of a monolith, packed bed, and expanded bed, the separation procedure is generally performed according to a conventional chromatography using a concentration gradient. In a case of the pure suspension, a batch process is used. The support of the present invention is preferably a filler. Alternatively, the support may be in the state of a chip, capillary, or a filter. As the solid phase support, magnetic particles may be used. The magnetic particle is not particularly limited so long as it can be easily magnetized by magnetic induction, and may include, for example, metals such as magnetite ($Fe_3O_4$), iron sesquioxide ($\gamma$-$Fe_2O_3$), various ferrites, iron, manganese, nickel, cobalt, and chromium; magnetic particles containing an alloy with cobalt, nickel, or manganese; hydrophobic or hydrophilic polymers containing the magnetic substance described above inside thereof, and the like. Preferable examples thereof may include magnetic particles, described in JP 2008-32411 A, in which a hydrophobic first polymer layer is formed on a surface of a mother particle containing superparamagnetic particles; a second polymer layer having glycidyl groups on at least surface thereof is formed on the first polymer layer; and the glycidyl group is chemically modified thereby to introduce one or more polar groups having at least one atom selected from the group consisting of an oxygen atom, nitrogen atom, and sulfur atom. In a preferable embodiment, affinity support of the present invention is a support for an affinity chromatography.

In one embodiment of the present invention, the solid phase support preferably has a particle size of from 20 to 200 µm. When the support is a synthetic polymer, the particle size is more preferably from 20 to 100 µm, even more preferably from 30 to 80 µm; and when the support is a polysaccharide, the particle size is more preferably from 50 to 200 µm, even more preferably from 60 to 150 µm. When the particle size is less than 20 µm, a column pressure is increased in a high flow rate condition, which do not have enough durability for practical use. When the particle size is more than 200 µm, a binding quantity of the immunoglobulin to the affinity support (binding capacity) may be inferior. The term "particle size" herein refers to a volume average particle diameter, obtained by using a laser diffraction scattering type particle size distribution measuring device.

In one embodiment of the present invention, the solid phase support is preferably porous and has a specific surface area of from 50 to 150 $m^2/g$, more preferably from 80 to 130 $m^2/g$. Here, when the specific surface area is less than 50 $m^2/g$, the binding capacity may sometimes be inferior, and when it is more than 150 $m^2/g$, the support is broken in a high flow rate condition because of the poor strength of the support, thus resulting in a possibility in which the column pressure may be increased. The term "specific surface area" herein refers to a value obtained by dividing a surface area of a pore having a pore size of from 10 to 5,000 nm, obtained by using a mercury porosimeter, by a dry weight of a particle.

In one embodiment of the present invention, the solid phase support preferably has a volume average pore size of from 100 to 1,400 nm. When the support is a synthetic polymer, it is more preferably from 100 to 400 nm, even more preferably from 200 to 300 nm, and when the support is a polysaccharide, it is more preferably from 500 to 1,400 nm, even more preferably from 800 to 1,200 nm. When the volume average pore size is less than 100 nm, the binding capacity may be remarkably reduced in a high flow rate condition, and when it is more than 1,400 nm, the binding capacity may be sometimes reduced regardless of the flow rate. The term "volume average pore size" herein refers to a volume average pore size of a pore having a pore size of 10 to 5,000 nm, obtained by using a mercury porosimeter When the solid phase support has a particle size, a specific surface area, and a pore size distribution, all of which are within the ranges described above, spaces between the particles, which are flow channels of a solution to be purified, and relatively large a pore size in the particle are optimally balanced with a binding surface area of the molecule to be purified, and the binding capacity is maintained at a high level in a high flow rate condition.

A material for the solid phase support is, for example, a polymer having a hydrophilic surface, which is, for example, a polymer having a hydroxyl group (—OH), a carboxyl group (—COOH), an aminocarbonyl group (—$CONH_2$ or an N-substituted type), an amino group (—$NH_2$ or a substituted type), or sn oligo or polyethyleneoxy group on an outer surface (and on an inner surface, if present) thereof. In one embodiment, the polymer may include synthetic polymers such as polymethacrylate, polyacrylamide, polystyrene, and polyvinyl alcohol, preferably synthetic polymers such as copolymers cross-linked by polyfunctional monomer such as polyfunctional (meth)acrylate or divinyl benzene. Such synthetic polymers can be easily produced in a known method (for example, see a method described in J. MATER. CHEM 1991, 1 (3), 371-374). Alternatively, commercially available produces such as TOYOPEARL (Tosoh Corporation) may be used. Polymers in other embodiments may include polysaccharides such as dextran, starch, cellulose, pullulan, and agarose. Such polysaccharides can be easily produced in a known method (for example, see a method described in Japanese Patent No. 4081143). Alternatively, commercially available products such as Sepharose (GE Healthcare Bioscience Corporation) may be used. In other embodiments, inorganic supports such as silica and zirconium oxide may be used.

In one embodiment of the present invention, one example of the porous particle used as the solid phase support may be exemplified by porous organic polymer particles containing a copolymer having 20 to 50% by mass of a cross-linkable vinyl monomer, 3 to 80% by mass of an epoxy group-containing vinyl monomer, and 20 to 80% by mass of a diol group-containing vinyl monomer, and having a particle size of from 20 to 80 µm, a specific surface area of from 50 to 150 $m^2/g$, and a volume average pore size of from 100 to 400 nm.

The pore having a pore size of from 10 to 5,000 nm, obtained by measurement of the solid phase support using a mercury porosimeter has preferably a penetration volume (pore volume) of from 1.3 to 7.0 mL/g. When the support is a synthetic polymer, it is more preferably from 1.3 to 2.5 mL/g, and when the support is a polysaccharide, it is more preferably from 3.0 to 6.0 mL/g.

1.1.2. Binding to Ligand

Binding of the ligand to the solid phase support can be performed in a general method for immobilizing the protein to the support. The immobilizing methods may include, for example, physical adsorption of the ligand to the support, chemical binding of the ligand to the support, and the like. Covalent binding may be exemplified as a method for chemically binding the ligand with the support. For example, a linker in the ligand covalently binds to the support through a carboxyl group, an amino group, or a hydroxyl group or a thiol group therein. A reactive group for the covalent binding may be introduced into the support. As the reactive group, a carboxyl group, an amino group, a hydroxyl group, a maleimide group, and an epoxy group are preferable, and among them, an epoxy group is more preferable because the reaction with the ligand proceeds in gentle conditions. Concrete examples of the method for binding the ligand to the support may include a method in which using a support having a carboxyl group, the carboxyl group is activated with N-hydroxysuccinimide, and it is reacted with an amino group in a ligand; a method in which using a support having an amino group or carboxyl group, it is reacted with a carboxyl group or an amino group in a ligand in the presence of a dehydration condensation agent such as water-soluble carbodiimide to form an amide binding; a method in which using a support having a hydroxyl group, the hydroxyl group is activated with a cyanogen halide such as cyanogen bromide, and it is reacted with an amino group in a ligand; a method in which a hydroxyl group in a support is tosylated or tresylated, and it is reacted with an amino group in a ligand; a method in which using a support having a maleimide group, it is reacted with a thiol group in a ligand to form a thioether binding; a method in which an epoxy group is introduced into a support using bisepoxide or epichlorohydrin, and it is reacted with an amino group, a hydroxyl group, or a thiol group in a ligand; a method in which using a support having an epoxy group, it is reacted with an amino group, a hydroxyl group, or a thiol group in a ligand, and the like. Of those above, the binding method in which the ligand is introduced through the epoxy group is desirable in terms of the safety in an aqueous solution in which the reaction is carried out.

An alcoholic hydroxyl group, which is a ring-opened epoxy group produced by ring-opening of an epoxy group, hydrophilizes a surface of the support to prevent a non-specific adsorption such as adsorption with a protein, and at the same time, improves toughness of the support in water, to prevent breakage of the support in a high flow rate condition. When residuary epoxy groups which are not bound to the ligand exist in the support after the immobilization of the ligand, accordingly, it is preferable to ring-open the residuary epoxy groups. The method for ring-opening the epoxy group in the support may be exemplified by a method in which the support is agitated in a water medium under heating or a room temperature using an acid or alkali. The epoxy group may be ring-opened with a mercapto group-containing blocking agent such as mercaptoethanol or thioglycerol, or an amino group-containing blocking agent such as monoethanol amine. The most preferable ring-opened epoxy group is a ring-opened epoxy group obtained by ring-opening of the epoxy group contained in the support using thioglycerol. The thioglycerol has advantages in which the toxicity is lower than that of, for example, mercaptoethanol as a starting material, the ring-opened epoxy group added with the thioglycerol has a lower non-specific adsorption than that of a ring-opened group obtained using an amino group-containing blocking agent, and a dynamic binding quantity of the support is increased.

1.2. Ligand
1.2.1. Linker

A protein ligand, contained in the affinity support of the present invention, contains a linker R and a protein ligand $R^1$, and represented by the following general formula (1):

$$R-R^1 \qquad (1)$$

When the protein ligand is reacted with, for example, an epoxy group on the support, as described above, the ligand can be immobilized on the support.

The linker R in formula (1) described above is a linker containing, at one end thereof, a functional group which is reactive with a reactive functional group in a solid phase support. The linker can be used for linking a protein $R^1$ showing affinity to immunoglobulin, described below, to a support to immobilize it. The linker is used for efficiently immobilizing $R^1$ on the support; whereas, the linker is appropriate for substantially maintaining the immunoglobulin affinity of $R^1$. When the linker is used, accordingly, the protein $R^1$ can be more efficiently introduced, for example, 25% or more introduced to the support, compared to a case in which the linker is not used. In addition, the protein $R^1$, which is efficiently introduced using the linker, can maintain its activity, for example an immunoglobulin-binding property, on the support.

In one embodiment, the linker R has preferably a length of from 0.9 nm to 91 nm, more preferably from 1.8 nm to 15.4 nm, even more preferably from 3.6 nm to 7.3 nm. Here, the length of the linker refers to a distance from a site binding to $R^1$ to a site binding the solid phase support in the three-dimensional structure of the linker. In one embodiment, the linker has a helical structure, and the full length of the helical structure has the length described above.

The linker R is preferably a peptide linker containing at least two proline residues. The linker R is more preferably a polypeptide containing at least two proline residues and an amino acid residue having an amino group or a thiol group on the side chain. The linker R is even more preferably a polypeptide containing at least two proline, and containing preferably at least one, more preferably one or more cysteine (C) or lysine (K) residue(s) at the terminal binding to the solid phase support. When the linker R contains multiple cysteine residues, it is necessary to take care so as not to form a disulfide binding between the cysteine residues, and in order to avoid the formation of the disulfide binding between the cysteine residues, it is preferable, for example, to use a reducing agent. The reducing agent is not particularly limited so long as it can reduce the disulfide binding, and may include, for example, 2-mercaptoethanol, dithiothreitol, 1-thioglycerol, tris(2-carboxyethyl)phosphine hydrochloride, and the like.

In a preferable embodiment, the linker R contains a polyproline having at least three successive proline residues. The number of the proline residues contained in the polyproline is preferably from 3 to 300, more preferably from 6 to 51, even more preferably from 12 to 24. The polyproline can form a polyproline helix in which three proline residues form one unit, and thus the linker R can contain a polyproline helix having preferably 3 to 300, more preferably 6 to 51, even more preferably 12 to 24 proline residues. In other words, about one rotation (which may also refer to one pitch in the present specification) of the polyproline helix is formed from three proline residues, and thus the linker R can contain a polyproline helix having preferably 1 to 100 pitches, more preferably 2 to 17 pitches, even more preferably 4 to 8 pitches. In the present invention, however, the number of pitches of the polyproline helix in the linker R is not limited to an integer. The polyproline helix has a length per pitch of about 0.9 nm (J. AM. CHEM. SOC., 2007, 129 (4): 873-880).

In a more preferable embodiment, the linker R may contain, in addition to the polyproline, one or more amino acid residues other than the proline. The linker R contains preferably one or more amino acid residues other than the proline between the polyproline and a linker terminal binding to the solid phase support, more preferably one or more amino acid residues having an amino group or a thiol group between the polyproline and a linker terminal binding to the solid phase support. The amino acid residue other than the proline is preferably 1 to 3 cysteine (C) or lysine (K) residues. It is preferable that the linker R is a linker containing at least one, more preferably 1 to 3 cysteine (C) or lysine (K) residues at the terminal binding to the solid phase support, and a polyproline having 3 to 300, more preferably 6 to 51, even more preferably 12 to 24 proline residues.

1.2.2. Immunoglobulin-Binding Protein $R^1$ in formula (1) described above is a protein showing affinity to immunoglobulin (or immunoglobulin-binding protein). Examples of $R^1$ may include proteins containing at least one immunoglobulin-binding domain selected from the group consisting of Fc-binding proteins which bind to an immunoglobulin Fc region, and immunoglobulin-binding domains derived from Protein A. $R^1$ may contain any number of immunoglobulin-binding domains so long as it has no industrial problems.

$R^1$ preferably contains at least one immunoglobulin-binding domain derived from Protein A. More preferably, $R^1$ contains at least one immunoglobulin-binding domain selected from the group consisting of an A domain, a B domain, a C domain, a D domain, an E domain, and a Z domain of Protein A, and mutants thereof.

The mutants of the above A to E and Z domains can be produced by addition, deletion, substitution or deficiency of an amino acid residue to or from the A to E and Z domain of Protein A, or modification such as chemical modification of the amino acid residue. The addition, deletion, substitution, or the deficiency of the amino acid residue can be performed in a known process such as a site-specific mutation to polynucleotide encoding the domain described above.

In one preferable embodiment, $R^1$ contains at least one immunoglobulin-binding domain selected from the group consisting of immunoglobulin-binding domains containing an amino acid sequence represented by SEQ ID NO: 1, immunoglobulin-binding domains containing a partial sequence of the amino acid sequence represented by SEQ ID NO: 1, and immunoglobulin-binding domains containing an amino acid sequence having at least 70% identity to the amino acid sequence represented by SEQ ID NO: 1.

In one preferable embodiment, $R^1$ contains at least one immunoglobulin-binding domain selected from the group consisting of immunoglobulin-binding domains containing an amino acid sequence represented by SEQ ID NO: 2, immunoglobulin-binding domains containing a partial sequence of the amino acid sequence represented by SEQ ID NO: 2, and immunoglobulin-binding domains containing an amino acid sequence having at least 70% identity to the amino acid sequence represented by SEQ ID NO: 2.

In one preferable embodiment, $R^1$ contains at least one immunoglobulin-binding domain selected from the group consisting of immunoglobulin-binding domains containing an amino acid sequence represented by SEQ ID NO: 3, immunoglobulin-binding domains containing a partial sequence of the amino acid sequence represented by SEQ ID NO: 3, and immunoglobulin-binding domains containing an amino acid sequence having at least 70% identity to the amino acid sequence represented by SEQ ID NO: 3.

In one preferable embodiment, $R^1$ contains preferably 2 or more, more preferably 2 to 12, even more preferably 3 to 8 of the immunoglobulin-binding domains described above. The immunoglobulin-binding domains may be the same or different. Each immunoglobulin-binding domain is preferably linked to a C terminal of an adjacent domain through the N terminal thereof. Each domain may be linked directly or through peptide having 1 to 10 amino acid residues to the adjacent domain.

In another embodiment, $R^1$ only needs to contain one or more immunoglobulin-binding domains described above, the number of which is preferably 10 or less, more preferably 2 or more and 8 or less, even more preferably 4 or more and 6 or less, in terms of immunoglobulin-binding capacity, and productivity of the immunoglobulin-binding protein.

It is preferable that the immunoglobulin-binding domain contained in $R^1$ have a Val residue at a position corresponding to the position 1 of an amino acid sequence represented by SEQ ID NO: 1, 2, or 3 and/or have an Ala residue at position corresponding to the position 29 of an amino acid sequence represented by SEQ ID NO: 1, 2, or 3.

Examples of preferable $R^1$ may include polypeptide containing an amino acid sequence represented by SEQ ID NO: 4. The amino acid sequence represented by SEQ ID NO: 4 is a polypeptide containing 4 immunoglobulin-binding domains containing an amino acid sequence in which AL at the position 1 of an amino acid sequence represented by SEQ ID NO: 3 is substituted by Val and Gly at the position 29 is substituted by Ala.

Examples of other preferable $R^1$ may include a polypeptide having at least 70% identity to an amino acid sequence represented by SEQ ID NO: 3, and containing 3 to 8 immunoglobulin-binding domains containing an amino acid sequence having Val at a position corresponding to the 1st position of SEQ ID NO: 3 and Ala at a position corresponding to the position 29.

In general protein ligands, a linker can be bound or fused to its terminal to substantially maintain the functions of the immunoglobulin-binding protein. The linker R is, accordingly, preferably bound to the C-terminal or N-terminal of the amino acid sequence in the immunoglobulin-binding protein $R^1$. Alternatively, two linkers R may be each bound to both terminals of the amino acid sequence in $R^1$, or the linker R may be bound to an amino acid residue, which is not a terminal residue of the amino acid sequence in $R^1$.

1.2.3. Production of Ligand

The protein ligand R—$R^1$ represented by formula (1) described above, contained in the affinity support of the present invention, is a fusion polypeptide containing the linker R and the immunoglobulin-binding protein $R^1$. As described above, $R^1$ contained in the protein ligand is a fusion polypeptide containing one or more, preferably 2 to 12, more preferably 3 to 8 immunoglobulin-binding domains. The fusion polypeptide can be produced in a recombinant method which is known in the art.

As a standard technology for producing the protein ligand described above, a known gene recombination technology described in, for example, Frederick M. Ausbel et al., Current Protocols in Molecular Biology, or Molecular Cloning edited by Sambrook et al. (Cold Spring Harbor Laboratory Press, 3rd edition, 2001), or the like, can be utilized. Expression vectors containing nucleic acid sequence encoding the protein ligand described above are transformed into host such as E. coli, and the obtained recombinants are cultivated in an appropriate liquid culture medium, whereby a large amount of a desired protein ligand can be economically obtained from the cultured cells. As a preferable expression vector, any already known vector capable of replicating in a host cell can be used. It may include, for example, plasmid described in the specification of U.S. Pat. No. 5,151,350, or plasmid described in Molecular Cloning edited by Sambrook et al. (Cold Spring Harbor Laboratory Press, 3rd edition, 2001). The host used for the transformation is not particularly limited, and known hosts used for expression of a recombinant protein can be used such as bacteria such as E. coli, fungi, insect cells, and mammalian cells. In order to transform the host by introducing a nucleic acid into the host, any method which is known in the art can be used according to each host, and a known method described in, for example, Molecular Cloning edited by Sambrook et al. (Cold Spring Harbor Laboratory Press, 3rd edition, 2001) can be utilized. A method for recovering the protein, expressed by cultivation of the transformed recombinant (bacteria, for example), is well-known by those skilled in the art, and is described in Examples of the present invention.

The present invention also provides polynucleotide (DNA, for example) encoding the protein ligand R—$R^1$ represented by formula (1) described above, a vector containing the same, and a recombinant containing the same.

The affinity support of the present invention can be produced by binding or fusing the linker R to the immunoglobulin-binding protein $R^1$ to obtain a fusion polypeptide R—$R^1$, and then immobilizing it on the solid phase support. Alternatively, the affinity support may be obtained by binding the linker R to the solid phase support by using a chemical method, recombinant method, or an enzyme before the linker is bound to the immunoglobulin-binding protein $R^1$, and then binding $R^1$ to the linker R. The appropriate solid phase support for binding to the linker R is as described in item 1.1 above.

1.3. Effects

The affinity support according to one embodiment of the present invention has a large amount of ligand immobilized on the support, and a high initial TgG static binding capacity (SBC), and thus has a high effective utilization rate E [%], calculated according to the following formula, of the immunoglobulin-binding protein.

$E[\%]=[(SBC/\text{molecular weight of antibody})/(\text{amount of immunoglobulin-binding protein introduced}/\text{molecular weight of immunoglobulin-binding protein})] \times 100$ 2. Method for Isolating Immunoglobulin A method for isolating immunoglobulin according to one embodiment of the present invention will be explained. The method for isolating immunoglobulin according to the embodiment contains a step in which a sample containing immunoglobulin is brought into contact with the affinity support on which the protein ligand R—$R^1$, represented by formula (1), is immobilized to adsorb the immunoglobulin onto the support (a first step); and a step in which the immunoglobulin is eluted from the support (a second step), preferably further contains a step in which the support is washed with an alkaline liquid (a third step) after the second step. The affinity support of the present invention, used in the method for isolating immunoglobulin of the present invention, may be in a state of suspension, in a state where it is filled in a column, or in a state of chip, capillary, or filter.

In the first step, the sample containing immunoglobulin is brought into contact with, for example, a column in which the affinity support is filled in a condition in which the immunoglobulin is adsorbed onto the ligand. In the first step, almost all of substances other than the immunoglobulin in the sample are not adsorbed by the ligand nor do remain on the support. After that, if necessary, in order to remove a part of the substances weakly held on the ligand, the support may be washed with a neutral buffer containing a salt such as NaCl.

In the second step, an appropriate buffer of pH of 2 to 5 to elute the immunoglobulin adsorbed onto the ligand. The eluate is recovered, whereby the immunoglobulin can be isolated from the sample.

In the method for isolating immunoglobulin according to the embodiment, the third step is preferably performed subsequently to the second step. In the third step, the support is washed with an alkaline liquid (CIP washing). The alkaline liquid used in the third step may include, for example, an aqueous sodium hydroxide solution, aqueous potassium hydroxide solution, triethyl amine, tetrabutyl ammonium hydroxide, and the like.

The affinity support of the present invention can stably maintain the immunoglobulin-binding capacity even after the washing in the third step, and thus it can be repeatedly used in the method for isolating immunoglobulin of the present invention.

In one embodiment of the method for isolating immunoglobulin of the present invention, immunoglobulin to be isolated can be an antibody or a pharmaceutical composition containing the same. In one embodiment, accordingly, the present invention provides a method for producing an antibody preparation using the affinity support of the present invention. The procedure of the method is basically the same as in the method for isolating immunoglobulin isolate described above except that the sample containing a target antibody preparation is used.

EXAMPLE

The present invention is more specifically explained by means of Examples below. The following descriptions generally show embodiments of the present invention, and the present invention is not limited to the descriptions if there is no special reason.

Reference Example 1

Synthesis of Porous Particle

In 245.8 g of 2-octanone (manufactured by Toyo Gose Co., Ltd.) and 62 g of acetophenone (manufactured by Wako Pure Chemical Industries, Ltd.) were dissolved 8.2 g of glycidyl methacrylate (manufactured by Mitsubishi Rayon Co., Ltd.), 65.9 g of trimethylolpropane trimethacrylate (manufactured by Sartomer Corporation), and 90.6 g of glycerin monomethacrylate (manufactured by NOF Corporation), to which 2 g of 2,2'-azoisobutyronitrile (manufactured by Wako Pure Chemical Industries, Ltd.) to prepare an organic monomer solution.

Then, 8.5 g of polyvinyl alcohol (PVA-217 manufactured by Kuraray Co., Ltd), 0.43 g of sodium dodecyl sulfate (Emal 10G manufactured by Kao Corporation), and 21.3 g of sodium sulfate (manufactured by Wako Pure Chemical Industries, Ltd.) were added to 4,240 g of pure water, and the mixture was stirred over night to prepare an aqueous solution.

Next, the obtained solution was thrown into a 7 L separable flask, to which a thermometer, mixing impellers, and a condenser tube were attached, and it was set in a hot water bath. The stirring was started at 600 rpm in a nitrogen atmosphere. Subsequently, the separable flask was heated with the hot water bath, and the organic monomer solution was added to the resulting aqueous solution through a dropping funnel when the temperature of the aqueous solution reached 85° C., and the mixture was stirred for 5 hours.

Subsequently, the reaction liquid was cooled, and then moved to a 5 L propylene bin. It was allowed to stand until particles floated, and excess water was drawn out from below and discarded. Acetone was added to the reaction liquid to precipitate the particles. Next, the reaction liquid was allowed to stand for 3 minutes, and acetone was removed by decantation. This procedure was repeated twice, and then water was added to the liquid to precipitate the particles. Further, the liquid was allowed to stand for 3 minutes, and the decantation was performed. This procedure was repeated twice to wash the particles. The dispersion of the particles was substituted by acetone again, and it was air-dried over night. After that, drying with a vacuum dryer was performed to obtain 90 g of porous particles (hereinafter referred to as "PB1"). PB1 had a volume average particle size, according to a light scattering method, of 53 μm, and a specific surface area, according to a mercury porosimeter measurement, of 95 m²/g.

Comparative Example 1

(1) Preparation of Recombinant Immunoglobulin-Binding Protein

A plasmid encoding an amino acid sequence (SEQ ID NO: 4) of an immunoglobulin-binding protein and having no linker was prepared by a chemical synthesis, and it was introduced into *E. coli* BL21 (manufactured by STRATA-GENE), and transformation was performed. The transformed *E. coli* was incubated at 37° C. until an optical density (OD 600) reached about 10, and then IPTG (manufactured by Sigma-Aldrich) was added thereto so as to get a final concentration of 1 mM. Then incubation was performed at 37° C. for another 4 hours to express a recombinant immunoglobulin-binding protein. After the expression of the protein, cells were recovered, and they were crushed using lysozyme in a Tris buffer having a pH of 9.5. The recombinant immunoglobulin-binding protein was purified from the obtained *E. coli* crush liquid containing the recombinant immunoglobulin-binding protein using an anion exchange chromatography (Q-Sepharose FF manufactured by GE Healthcare Bioscience Corporation) and a cation exchange chromatography (SP-Sepharose FF manufactured by GE Healthcare Bioscience Corporation). The purified immunoglobulin-binding protein was dialyzed for 16 hours against a 10 mM citric acid buffer having a pH of 6.6. The immunoglobulin-binding protein had a purity of 95% or more, confirmed by SDS-PAGE. A theoretical molecular weight [kDa] of the immunoglobulin-binding protein was obtained using ExPACy ([www.expasy.org/compute_pi/]).

(2) Immobilization of Immunoglobulin-Binding Protein to Support

In 150 μL of pure water was suspended 8 mg of PB1, prepared in Reference Example 1, and the mixture was moved to a filter tube (manufactured by Millipore Ltd.). Centrifugation was performed to remove pure water. To this tube was added 450 μL of 0.1 M carbonic acid buffer (pH 9.8) containing 0.85 M sodium sulfate in which 1 mg of the recombinant immunoglobulin-binding protein, prepared in (1), was dissolved, and the mixture was shaken at 25° C. for 5 hours, whereby the immunoglobulin-binding protein was bound to PB1. After the produced particles were filtered, they were mixed with 450 μL of IM thioglycerol, and the reaction was performed at 25° C. for 16 hours to block remaining epoxy groups. The mixture was washed with 0.5 M of NaOH, followed by a 0.1 M sodium citrate buffer (pH 3.2), and finally 400 μL of phosphate buffered saline (BupH™ Modified Dulbecco's PBS, manufactured by PIERCE Corporation) was added thereto and porous particles immobilized with the immunoglobulin-binding protein were dispersed, to give 400 μL of a suspension liquid of the particles.

Comparative Example 2

A recombinant immunoglobulin-binding protein was prepared in the same manner as in Comparative Example 1 except that *E. coli* BL21 was transformed using a plasmid encoding an amino acid sequence (SEQ ID NO: 5) of immunoglobulin-binding protein containing a cysteine linker shown in Table 1. Then, the obtained protein was immobilized on the porous particle PB1.

Comparative Example 3

A recombinant immunoglobulin-binding protein was prepared in the same manner as in Comparative Example 1 except that *E. coli* BL21 was transformed using a plasmid encoding an amino acid sequence (SEQ ID NO: 6) of immunoglobulin-binding protein containing a polylysine linker shown in Table 1. Then, the obtained protein was immobilized on the porous particle PB1.

Example 1

A recombinant immunoglobulin-binding protein was prepared in the same manner as in Comparative Example 1 except that *E. coli* BL21 was transformed using a plasmid encoding an amino acid sequence (SEQ ID NO: 7) of immunoglobulin-binding protein containing a polyproline linker shown in Table 1. Then, the obtained protein was immobilized on the porous particle PB1.

Example 2

A recombinant immunoglobulin-binding protein was prepared in the same manner as in Comparative Example 1 except that *E. coli* BL21 was transformed using a plasmid encoding an amino acid sequence (SEQ ID NO: 8) of immunoglobulin-binding protein containing a polyproline linker shown in Table 1. Then, the obtained protein was immobilized on the porous particle PB1.

Example 3

A recombinant immunoglobulin-binding protein was prepared in the same manner as in Comparative Example 1 except that *E. coli* BL21 was transformed using a plasmid encoding an amino acid sequence (SEQ ID NO: 9) of immunoglobulin-binding protein containing a polyproline linker shown in Table 1. Then, the obtained protein was immobilized on the porous particle PB1.

Example 4

A recombinant immunoglobulin-binding protein was prepared in the same manner as in Comparative Example 1 except that *E. coli* BL21 was transformed using a plasmid encoding an amino acid sequence (SEQ ID NO: 10) of immunoglobulin-binding protein containing a polyproline linker shown in Table 1. Then, the obtained protein was immobilized on the porous particle PB1.

Example 5

A recombinant immunoglobulin-binding protein was prepared in the same manner as in Comparative Example 1 except that *E. coli* BL21 was transformed using a plasmid encoding an amino acid sequence (SEQ ID NO: 11) of immunoglobulin-binding protein containing a polyproline linker shown in Table 1. Then, the obtained protein was immobilized on the porous particle PB1.

Comparative Example 4

Epoxy groups were ring-opened by reacting the particles PB1, prepared in Reference Example 1, with an excess amount of thioglycerol, and then the resulting particles were reacted with 1,4-bis(2,3-epoxypropoxy) butane (BDDGE) (having 10 carbon atoms) in a molar quantity the same as that of the hydroxyl groups on the surface, thereby introducing linkers having a carbon chain. The obtained particles were referred to as "PB2." The recombinant immunoglobulin-binding protein (SEQ ID NO: 4) was immobilized on 8 mg of the particles PB2 in the substantially same manner as in Comparative Example 1 to obtain 400 μL of a suspension liquid of the particles.

Comparative Example 5

Epoxy groups were ring-opened by reacting the particles PB1, prepared in Reference Example 1, with an excess amount of thioglycerol, and then the resulting particles were reacted with 1,2-bis(2,3-epoxypropoxy) ethane (EGDG) (having 8 carbon atoms) in a molar quantity the same as that of the hydroxyl groups on the surface, thereby introducing linkers having a carbon chain. The obtained particles were referred to as "PB3." The recombinant immunoglobulin-binding protein (SEQ ID NO: 4) was immobilized on 8 mg of the particles PB3 in the substantially same manner as in Comparative Example 1 to obtain 400 μL of a suspension liquid of the particles.

TABLE 1

|  | Solid phase support | SEQ ID NO | Ligand Theoretical molecular weight [kDa] | Linker | The number of proline residues | Theoretical length of proline part (nm) |
|---|---|---|---|---|---|---|
| Comparative Example 1 | PB1 | 4 | 28.0 | None | 0 | — |
| Comparative Example 2 |  | 5 | 27.9 | C | 0 | — |
| Comparative Example 3 |  | 6 | 28.2 | KKK | 0 | — |
| Example 1 |  | 7 | 28.5 | PPPPPPC | 6 | 1.8 |
| Example 2 |  | 8 | 28.8 | PPPPPPPPPC | 9 | 2.7 |
| Example 3 |  | 9 | 29.3 | PPPPPPPPPPPPC | 12 | 3.6 |
| Example 4 |  | 10 | 29.6 | PPPPPPPPPPPPPPPPPPC | 18 | 5.4 |
| Example 5 |  | 11 | 29.9 | PPPPPPPPPPPPPPPPPPKKK | 18 | 5.4 |
| Comparative Example 4 | PB2 | 4 | 28.0 | carbon chain C10 | 0 | — |
| Comparative Example 5 | PB3 | 4 | 28.0 | carbon chain C8 | 0 | — |

Experimental Example 1

Measurement of Amount of Ligand Binding Amount

From 400 μL of the suspension liquid of the particles from each Example 1 to 5 and Comparative Example 1 to 5 was taken 50 μL of the suspension liquid. Using a BCA Assay kit (PIERCE Corporation), an amount of the immunoglobulin-binding protein, which bound to the particle, was measured, and a relative value to a binding amount in Comparative Example 1, which was assumed as 100, was obtained.

Experimental Example 2

Measurement of Static Binding Capacity of Immunoglobulin G (IgG)

From 400 μL of the suspension liquid of the particles from each Example 1 to 5 and Comparative Example 1 to 5 was taken 150 μL of the suspension liquid, and each was thrown into a filter tube (Millipore Ltd.). Into the tube was poured 300 μL of 0.1 M phosphate buffer (pH 7.5) containing 5 mg of IgG, and the mixture was shaken at 25° for one hour to adsorb IgG onto the particles. After centrifugation, the particles were washed with 450 μL of 0.1 M phosphate buffer having a pH of 7.5, and IgG, adsorbing on the particles, was eluted using 0.1 M citric acid buffer having a pH of 3.2. A static binding capacity (SBC) of IgG of the particles was measured from an optical density of the eluate at 280 nm.

Experimental Example 3

Utilization Efficiency of Immunoglobulin-Binding Protein

An effective utilization rate E [%] of the immunoglobulin-binding protein in the porous particle from each Example 1 to 5 and Comparative Example 1 to 5 was calculated from the ligand binding amount and SBC measured in Experimental Example 1 and Experimental Example 2 according to the following formula:

$$E[\%] = [(SBC/\text{molecular weight of antibody})/(\text{amount of immunoglobulin-binding protein introduced}/\text{molecular weight of immunoglobulin-binding protein})] \times 100$$

The results in Experimental Examples 1 to 3 are shown in Table 2.

TABLE 2

|  | Ligand binding amount | | SBC [μg-IgG/mg particle] | Effective utilization rate E [%] |
|---|---|---|---|---|
|  | [μg/mg particle] | Relative value [%] | | |
| Comparative Example 1 | 54.2 | 100.0 | 251.3 | 89.6 |
| Comparative Example 2 | 62.3 | 115.0 | 344.4 | 106.3 |
| Comparative Example 3 | 62.9 | 116.1 | 340.9 | 105.3 |
| Example 1 | 73.2 | 135.1 | 348.2 | 93.4 |
| Example 2 | 73.5 | 135.7 | 355.9 | 96.0 |
| Example 3 | 72.6 | 134.0 | 360.1 | 100.4 |
| Example 4 | 72.7 | 134.2 | 384.5 | 108.1 |
| Example 5 | 74.2 | 137.0 | 375.4 | 104.4 |
| Comparative Example 4 | 45.6 | 84.2 | 230.6 | 97.7 |
| Comparative Example 5 | 50.7 | 93.6 | 241.0 | 91.8 |

The particles prepared in Examples 1 to 5, onto which the immunoglobulin protein containing the polyproline linker was immobilized, were more improved in the ligand binding amount and SBC than those in Comparative Examples 1 to 3. Moreover, there was a tendency that longer polyproline residue served to improve SBC and elevate utilization rate E [%]. As shown in Examples 4 and 5, the functional groups used for binding of the linker to support, derived from an amino group of lysine and a thiol group of cysteine, gave substantially the same introduction amounts. In contrast, as shown in Comparative Examples 5 and 6, the linker having the carbon chain did not contribute to improvement of the ligand binding amount or SBC at all.

The explanation concerning the embodiments of the present invention is described above. The present invention, however, is not limited to the embodiments described above, and can be variously modified. The present invention also encompasses substantially the same configurations as those in the embodiments explained above, (for example, a configuration which is the same in function, method and result, and a configuration having the same objective and result). The present invention also encompasses configurations whose non-essential part of the embodiments explained above is substituted. The present invention also encompasses configurations capable of exerting the same effects or achieving the same objectives as those in the embodiments explained above. The present invention also encompasses configurations in which a known technology is added to the configuration of the embodiments explained above.

The invention claimed is:

1. An affinity support, comprising:
a solid phase support and
a protein ligand,
wherein the protein ligand has the following formula(1):

R—R¹      (1), wherein
R is a linker binding to the solid phase support, which comprises a polyproline comprising from 12 to 24 proline residues, and
R¹ is a protein having an affinity to an immunoglobulin, and
R is bound to a C terminal or an N terminal of an amino acid sequence of the protein R¹.

2. The affinity support according to claim 1, wherein the linker has a length of from 3.6 nm to 7.3 nm.

3. The affinity support according to claim 1, wherein the linker comprises an amino acid residue having an amino group or a thiol group at a terminal binding to the solid phase support.

4. The affinity support according to claim 1, wherein the protein having the affinity to an immunoglobulin comprises an immunoglobulin-binding domain derived from an Fc-binding protein or Protein A.

5. The affinity support according to claim 1,
wherein the protein having the affinity to an immunoglobulin comprises at least one immunoglobulin-binding domain selected from the group consisting of
an immunoglobulin-binding domain consisting of the amino acid sequence of SEQ ID NO: 3,
an immunoglobulin-binding domain comprising a partial sequence of the amino acid sequence of SEQ ID NO: 3, and an immunoglobulin-binding domain consisting of an amino acid sequence having at least 70% identity to the amino acid sequence of SEQ ID NO: 3.

6. The affinity support according to claim 4, wherein the protein having the affinity to an immunoglobulin comprises two or more of the immunoglobulin-binding domains.

7. The affinity support according to claim 1, wherein the solid phase support comprises at least one reactive group capable of binding a thiol group or an amino group.

8. The affinity support according to claim 7, wherein the at least one reactive group is an epoxy group.

9. A method for isolating immunoglobulin, comprising:
isolating the immunoglobulin with the affinity support according to claim 1.

10. An affinity ligand, comprising:
a linker R and
a protein ligand $R^1$,
wherein
the linker R comprises a polyproline comprising from 12 to 24 proline residues,
$R^1$ is a protein having an affinity to an immunoglobulin, and
R is bound to a C terminal or an N terminal of an amino acid sequence of the protein $R^1$.

* * * * *